US008968677B2

(12) United States Patent
LaBorde et al.

(10) Patent No.: US 8,968,677 B2
(45) Date of Patent: Mar. 3, 2015

(54) FRAZIL ICE CONJUGATE ASSAY DEVICE AND METHOD

(71) Applicants: Ronald T. LaBorde, San Diego, CA (US); Nicholas J. Neild, Poway, CA (US)

(72) Inventors: Ronald T. LaBorde, San Diego, CA (US); Nicholas J. Neild, Poway, CA (US)

(73) Assignee: Quantum Design International, Inc., San Diego, CA (US)

( * ) Notice: Subject to any disclaimer, the term of this patent is extended or adjusted under 35 U.S.C. 154(b) by 235 days.

(21) Appl. No.: 13/747,199

(22) Filed: Jan. 22, 2013

(65) Prior Publication Data

US 2014/0205503 A1    Jul. 24, 2014

(51) Int. Cl.
  *G01N 21/75*    (2006.01)
  *G01N 33/50*    (2006.01)

(52) U.S. Cl.
  CPC ..................... *G01N 33/50* (2013.01)
  USPC ............ 422/420; 422/52; 422/73; 422/82.01; 422/82.05; 422/82.08; 422/82.09; 422/82.11; 422/400; 422/401; 422/422; 422/423; 422/424; 422/425; 422/426; 422/427; 422/428; 422/429; 422/68.1; 422/82.06; 422/407; 422/501; 422/502; 422/503; 422/504; 436/164; 436/177; 436/43; 436/63; 436/169; 436/170; 435/29; 435/4; 435/7.1; 435/13; 435/283.1; 435/287.1; 435/287.7; 435/287.8; 435/287.9; 435/288.7

(58) Field of Classification Search
  USPC ......... 422/52, 73, 82.01, 82.05, 82.08, 82.09, 422/82.11, 119, 102, 400, 401, 416, 420, 422/421, 422, 423, 424, 425, 426, 427, 428, 422/429, 68.1, 82.06, 407, 501, 502, 503, 422/504; 436/164, 177, 43, 63, 169, 170; 435/29, 4, 6, 7.1, 13, 283.1, 287.1, 435/287.7, 287.8, 287.9, 288.7
  See application file for complete search history.

(56) References Cited

U.S. PATENT DOCUMENTS 3,868,470 A    2/1975    Fallon et al.
4,168,146 A    9/1979    Grubb et al.
(Continued)

FOREIGN PATENT DOCUMENTS

EP    0383619 B1    8/1990
EP    0728310 B1    8/1996

OTHER PUBLICATIONS

R. Gruetzmacher et al., "Magnetic Immunoassay: A Heterogeneous Immunoassay Based on the Detection of Magnetic Particles," Clinical Chemistry, vol. 29, No. 6, p. 1252 (1983).
(Continued)

*Primary Examiner* — Dennis M White
(74) *Attorney, Agent, or Firm* — The Maxham Firm

(57) ABSTRACT

An improved apparatus and method for dispersion of a labeling conjugate in a diagnostic assay, the result being a one-step assay. By eliminating a conjugate pad as in conventional lateral diagnostic devices, and forming a frazil ice pellicle (FIP), rehydration and flow are improved resulting in better reproducibility, improved sensitivity, and reduced costs of individual assay devices. The formation of a frazil ice film formed on a super cooled surface of a sample receiving means simplifies assay assembly. Lyophilization of the FIP improves the release of a sample/analyte/label matrix into a macro channel as in a direct flow assay, while at the same time allowing reagents to mix and flow, thereby optimizing the assay performance. The reagents of the conjugate and the formation of the FIP stabilize the conjugate proteins and provide extended shelf life to the diagnostic assay device.

11 Claims, 4 Drawing Sheets

(56) References Cited

U.S. PATENT DOCUMENTS

| | | |
|---|---|---|
| 4,305,924 A | 12/1981 | Piasio et al. |
| 4,366,241 A | 12/1982 | Tom et al. |
| 4,632,901 A | 12/1986 | Valkirs et al. |
| 4,695,554 A | 9/1987 | O'Connell et al. |
| 4,703,017 A | 10/1987 | Campbell et al. |
| 4,956,302 A | 9/1990 | Gordon et al. |
| 5,026,562 A | 6/1991 | Schmidt et al. |
| 5,120,143 A | 6/1992 | Fujiwara et al. |
| 5,578,577 A | 11/1996 | Ching et al. |
| 5,591,645 A | 1/1997 | Rosenstein |
| 5,602,040 A | 2/1997 | May et al. |
| 5,622,871 A | 4/1997 | May et al. |
| 5,714,389 A | 2/1998 | Charlton et al. |
| 5,798,273 A | 8/1998 | Shuler et al. |
| 5,879,951 A | 3/1999 | Sy |
| 5,958,790 A | 9/1999 | Cerny |
| 5,989,921 A | 11/1999 | Charlton et al. |
| 5,998,220 A | 12/1999 | Chandler |
| 6,017,767 A | 1/2000 | Chandler |
| 6,046,585 A | 4/2000 | Simmonds |
| 6,485,982 B1 | 11/2002 | Charlton |
| 6,534,320 B2 | 3/2003 | Ching et al. |
| 6,607,922 B2 | 8/2003 | LaBorde |
| 7,323,139 B2 | 1/2008 | LaBorde et al. |
| 7,547,557 B2 | 6/2009 | LaBorde et al. |

OTHER PUBLICATIONS

J. Singer et al., "The Latex Fixation Test, Application to the Serologic Diagnosis of Rheumatoid Arthritis," American Journal of Medicine, pp. 888-892 (1956).

FRAZIL ICE CONJUGATE ASSAY DEVICE AND METHOD

FIELD OF INVENTION

The concept described herein relates generally to diagnostic assays, and more specifically to a lateral flow assay device with improved conjugate delivery and manufacturability.

DISCUSSION OF RELATED ART

Various chromatographic assay techniques have been available for many years. Tests that can be performed with such chromatographic systems are, among others, immunoassays, which depend on the specific interaction between an antigen or hapten, and a corresponding antibody. Immunoassays have been used as a means of testing for the presence or amount, or both, of clinically important molecules and cells for some time. Immune-based latex agglutination tests for detecting a factor associated with rheumatoid arthritis were used as early as 1956 (Singer et al., Am. J. Med. 22:888-892 (1956)).

Among the many analytical systems used for detection of analytes, particularly analytes of biological interest, are direct flow and lateral flow chromatographic assay systems. Among the analytes frequently assayed with such systems are: (1) hormones, such as human chorionic gonadotropin (hCG), which is frequently assayed as a marker of human pregnancy; (2) antigens, particularly antigens specific to bacterial, viral, and protozoan pathogens, such as *streptococcus*, hepatitis virus, and *giardia*; (3) antibodies, particularly antibodies induced as a result of infection with pathogens, such as antibodies to the bacterium *helicobacter pylori* and to human immunodeficiency virus (HIV); (4) other proteins, such as hemoglobin, frequently assayed in determinations of fecal occult blood, an early indicator of gastrointestinal disorders such as colon cancer; (5) enzymes, such as aspartate aminotransferase, lactate dehydrogenase, alkaline phosphatase, and glutamate dehydrogenase, frequently assayed as indicators of physiological function and tissue damage; (6) drugs, both therapeutic drugs, such as antibiotics, tranquilizers and anticonvulsants, and illegal drugs of abuse, such as cocaine, heroin, and marijuana; (7) vitamins; (8) nucleic acid material; and (9) biological markers for many illnesses or events such as MI in the use of ProBNP, tropinin and CRP, or for cancer using PSA or other cancer markers. Other markers can be used that pertain to the diagnosis of cancer and the therapeutic monitoring of the disease. There are assays designed and formulated for environmental contaminants, food toxins, biowarfare agents, and veterinary applications using lateral flow technology.

Such chromatographic systems are frequently used by physicians and medical technicians for rapid in-office diagnosis, commonly referred to as "point of care" (POC) devices, and therapeutic monitoring of a variety of conditions and disorders. They are also increasingly used by: patients themselves for at-home monitoring of medical conditions and disorders; parole officers for workplace drug monitoring; scientists for use in field testing for transgenic crops and environmental contaminants; soldiers in battlefield conditions for biological warfare weapon detection; and veterinary and emergency technicians for quick testing, where rapid results are needed.

Included in the chromatographic techniques used in conjunction with immunoassays is a procedure known as immunochromatography. In general, this technique uses a labeling reagent or particle that has been linked to an antibody, antigen peptide, or ligand for the molecule to be assayed, forming a conjugate. This conjugate is then mixed with a specimen and, if the molecule to be assayed is present in the specimen, the labeling reagent-linked complex binds to the molecule to be assayed, thereby giving an indication that the molecule to be assayed is present. The labeling reagent or particle can be identifiable by color, reflection, absorption, magnetic properties, radioactivity, fluorescence, chemilluminescence, specific reactivity with another molecule, or some other physical or chemical property. The specific reactions that are employed vary with the nature of the molecule being assayed and the sample to be tested. After labeling it can then be measured and quantified. The use of magnetic particles for labels and, specifically, lateral flow diagnostic labels, has been disclosed (Gruetzmacher et al., Magnetic Immunoassay: A Heterogeneous Immunoassay Based on the Detection of Magnetic Particles (AACC Chicago 1983)). Specifically, a technique and instrument to detect the magnetic signature of the accumulation of magnetic particles is disclosed in U.S. Pat. No. 6,046,585, and a technique for implementation of the technology is taught in U.S. Pat. No. 6,607,922.

Immunochromatographic assays fall into two principal categories: "sandwich" and "competitive," according to the nature of the antigen-antibody complex to be detected and the sequence of reactions required to produce that complex. In the case of antigen detection, the sandwich immunochromatographic procedures call for mixing the sample that may contain the analyte to be assayed with antibodies to the analyte. These antibodies are mobile and typically are linked to a label or a reagent, such as dyed latex beads, a colloidal metal sol, or a radioisotope. This mixture is then introduced to a portion of a bibulous membrane. The sample is delivered via capillary action from a sample pad onto a conjugate pad which has been infused and dried with a conjugate. The sample solution rehydrates the conjugate and is distributed onto a chromatographic medium or membrane containing bands or capture zones. These bands or capture zones contain immobilized antibodies for the analyte of interest or even for the capture of the label itself. The chromatographic medium can also be in the form of a strip resembling a dipstick and a liquid sample is then distributed to the conjugate pad by absorbing the sample. When the complex of the molecule to be assayed and the labeled antigen reaches the zone of the immobilized antibodies on the chromatographic medium, binding occurs, and the bound-labeled antibodies are localized at the zone. This indicates the presence of the analyte to be assayed. This technique can be used to obtain qualitative results. There are many embodiments of different combinations of antigens, antibodies, and markers, thus the namesake, "sandwich assay." Examples of sandwich immunoassays performed on test strips are described in U.S. Pat. Nos. 4,168,146, 4,366,241, 6,017,767, 5,998,220, and 4,305,924.

In competitive or indirect immunoassays, the immobilized component is present in controlled amounts and the mobile component is present in unknown amounts. The unknown amount of mobile component is supplemented with a known amount of the same component that has been tagged by the addition of a measurable constituent which does not interfere with its immunochemical reactive properties. The tag may consist of a radioisotope, a chromophor, a particle, a fluorophor, or an enzyme, for example. The amount of tagged material bound immuno-chemically to the solid phase will depend upon the amount of untagged component in solution competing for the same binding sites. The more of the unknown component present, the less will be the amount of bound tagged component.

Enzyme-based chromatographic assays are used in addition to immunochromatographic assays. These techniques are roughly analogous to immunochromatographic assays, but use an enzymatic-catalyzed reaction instead of an antigen-antibody reaction. The enzymatic-catalyzed reaction frequently generates a detectable product. Other analogous chromatographic assays are known. Although useful, currently available chromatographic techniques using test strips have certain limitations.

Typically one end of the test strip is exposed to the sample, normally a fluid of some type, being tested for the particular target analytes of interest. The fluid migrates through a sample pad, then onto a conjugate pad (that pad contains the colloidal label complex) and onto the chromatographic medium whereby the analyte with its label is captured and immobilized, while the remaining fluid is absorbed into a medium at the distal end of the assay strip.

Examples of lateral flow assay methods and apparatuses, where the reading is normally conducted optically, are shown in U.S. Pat. Nos. 4,632,901, 5,591,645, 5,602,040, 5,622,871, 5,714,389, 5,798,273, 5,879,951, and 5,958,790.

A limitation on chromatographic devices currently available for use by the clinician or technician is their inability to perform reliable quantitative assays. One of the reasons for this lack of performance is the poor distribution and reproducibility of the conjugate complex as it rehydrates within the conjugate pad or on the chromatographic medium. U.S. Pat. Nos. 5,120,143, 5,578,577, 6,534,320, 6,485,982, and 4,956,302 provide examples of devices and methods that demonstrate the problem. The labeled sandwich at the capture zone, or the decrease of label at the capture zone of a competitive assay, is read by detection of the label giving a suggestion of the concentration of the analyte, so any improvement in the conjugate delivery or efficiency improves the assay's ability to obtain quantitative results with lower coefficients of variation, sensitivity, and precision. Even so, quantitative accuracy is not characteristic of these devices or assays.

In the existing practice conjugate labels are impregnated into a fiberglass membrane or other coarse fiber material. The impregnation is either by immersing the fiberglass membrane ("conjugate pad") into a conjugate reagent and soaking the entire pad, or by spraying the material and having the conjugate reagent dispersed into the fibers of the pad, examples being U.S. Pat. Nos. 5,602,040, 4,695,554, and 4,703,017, among others.

In conventional lateral flow assays and construction, the "conjugate" is dried and impregnated within the fibers of the conjugate pad membrane and assembled into a lateral flow configuration. This is where the sample pad is overlapped onto the conjugate pad and the conjugate pad is overlapped onto the chromatographic medium (or analytical membrane). The conjugate pad is then used to deliver labels, "conjugate," typically colloidal gold, to a fluid phase that includes the analyte and the sample matrix. The fluid phase is driven by capillary action with a bibulous membrane to produce lateral flow of fluids from the sample pad through the conjugate pad to the analytical membrane and ultimately to an absorbent pad or wick. This dispersal design and model inhibits the usefulness of the lateral flow mechanism. There are many surface treatments of the conjugate pad typically used to enhance the release of the dried conjugate reagent (May, U.S. Pat. Nos. 5,602,040 and 5,622,871; Unilever/Unipath, EP0728310 B1). Coatings of sugars and the like are commonly used, as well as are other known reagents. These coatings interact with the fibers of the membrane and with each other. They also interact with the applied conjugate in that they dissolve and release unequally from the individual fibers, thereby inhibiting or possibly even defeating the purpose of their application. This uneven dissolution within the matrix of fibers releasing the conjugate labeled sample results in uneven flow and reproducibility, thereby making a true quantification of the analyte of interest difficult at best and more likely not usefully possible.

A different direct flow lateral flow assay device is shown in U.S. Pat. No. 7,547,557.

SUMMARY OF EMBODIMENTS OF THE INVENTION

Broadly speaking, embodiments of the invention relate to lateral flow assay technology. They may employ colloidal particles of all kinds, including magnetic colloids, to label the analyte of interest. Disclosed is a new device and a new process to place, store, maintain, and arrange mechanically within an assay the conjugate complex labels used for analyte detection.

A device constructed according to the principles of the invention includes at least one analytical membrane with a sample distribution means and a housing that allow a dehydrated conjugate complex to be retained, rehydrated, and delivered (associated analyte or analytes) to the chromatographic medium without a separate conjugate pad, thereby eliminating one of the five parts of a conventional lateral flow assay In one embodiment, the bound complexes of labeled particles and analytes are captured in predetermined areas or regions on the test strip and the presence and quantity of labeled analytes are then readable. In additional embodiments, the detection of analytes may be accomplished by visual means, since the complexes may also appear visually. The detection can be of fluorescence or chemiluminescence of the analyte label complex in which an instrument is needed to look at the photons of interest. Of significance is the fact that magnetic colloids can be detected and analyzed. In general, only at high concentrations can one visually observe the label. In most magnetic colloid assays the test region is visually unreadable and can be read only by an instrument particularly adapted for this purpose, such as the MagneticImmunochromatography Instrument Test System or Assay Development System of MagnaBioScience, LLC, San Diego, Calif.

More specifically, in preferred embodiments, what is disclosed is a lateral flow assay test device for quantitative detection of target analytes in a sample. Embodiments of the invention are directed to a new method and production of conjugate labels for lateral flow diagnostic assays.

Embodiments of the present invention relate to the sample pad portion of the assay test strip and the method by which the pad is formed and combined with a conjugate. In particular, they relate to a method of fanning super cooled surfaces to form a delicate structure in a manner which protects the structure and reduces degradation of the conjugate during processing and subsequent handling. This delicate structure is referred to as "frazil ice." Super cooled surfaces will encourage the formation of small ice crystals (frazil ice) on which a precisely controlled conjugate is sprayed. Examples related to frazil ice formation in the food industry are described in U.S. Pat. Nos. 3,868,470 and 5,026,562. Much of the relevant teaching can be found by reading the temperature profile techniques of this art form, which is used extensively in the frozen food industry.

In one embodiment of the invention, the test strip preferably has a cover layer to create a sealed assay. The central portion of the test strip has a polyester film base layer, preferably Mylar (a Du Pont trademark), plastic, or some equivalent material, with a pressure sensitive adhesive (PSA) layer on the base layer. A backed nitrocellulose layer is placed on top of the adhesive. On top of the nitrocellulose is a thin top cover that prevents contamination and, when used with a magnetic bead system, can be opaque, preventing the user from visually observing the test result.

The nitrocellulose layer (analytical membrane) preferably has at least two striped sections: a capture or test line, and a control line to ensure that the test has been preformed. The analytical lines can be multiplexed to quantify more than one analyte. There are many modes of this arrangement that can be made. The capture or test line and the control line are preferably at right angles to the lengthwise axis of the strip. The stripes preferably permeate the nitrocellulose layer and are approximately 1.0-0.6 mm in width. In one embodiment, a calibration line is placed on the top cover layer, rather than on the nitrocellulose. In additional embodiments, there may be an additional procedural control line along with the capture and magnetic index or control lines. In one embodiment, the minimum distance between any two adjacent lines is about 5 mm. This distance ensures that the detector reads only one line at a time. Therefore, it is contemplated that the distance between any two adjacent lines is determined by the limitation that the sensitivity of the instrument (detector) be such that it reads only one line at a time, which relates to the selectivity of the detector.

The principles of the invention are also directed to a method for conducting a lateral flow immunoassay with quantitative detection of target analytes in a sample. The method involves applying the sample to the sample pad at one end of a lateral flow test strip, coupling super paramagnetic conjugate particles residing below the sample pad, the super paramagnetic particles being treated to bind with any target analyte in the sample, the sample and conjugate flowing through a macro fluidic channel to the analytical membrane, capturing the bound complexes of analyte and super paramagnetic particles in the capture region of the porous analytical membrane as the sample and bound complexes move through that membrane by capillary action, inserting at least a portion of the test strip sideways into a magnetic reader device (see U.S. Pat. No. 7,323,139), reading the quantity of labeled analytes in the capture region, and providing an output representative of the quantity of labeled analytes in the capture region.

BRIEF DESCRIPTION OF THE DRAWING

The objects, features and advantages of the invention will be more clearly perceived from the following detailed description when read in conjunction with the accompanying drawing, wherein.

DETAILED DESCRIPTION OF THE PREFERRED EMBODIMENTS

Figure 1:
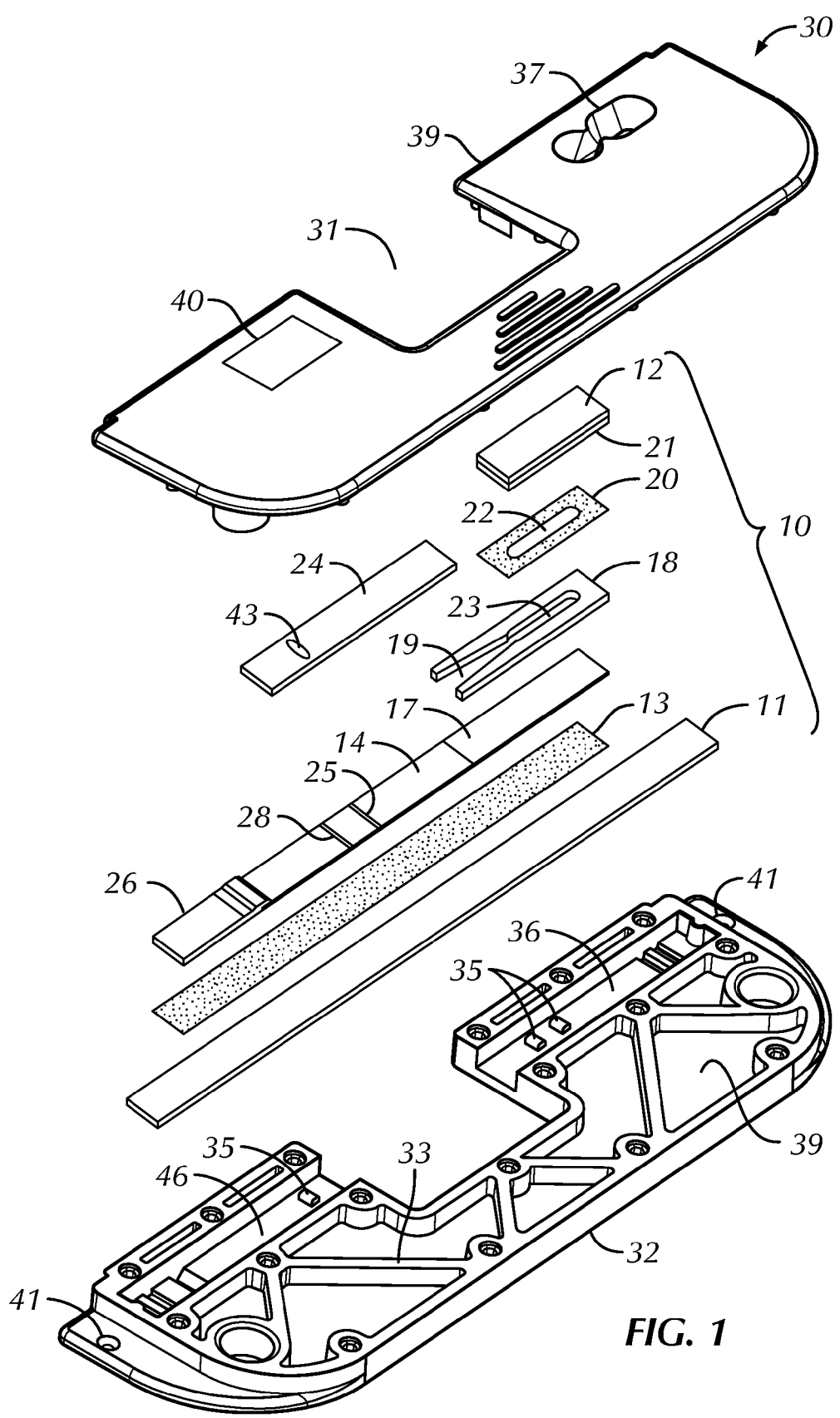
FIG. 1 is an exploded perspective view of a complete direct flow cassette with which an embodiment of the present invention is shown.

Advantages of the invention embodiments include that they have fewer elements, greatly improved reproducibility, lower coefficient of variation, and afford greater sensitivity for the assay device compared with known lateral flow techniques. It is a one-step assay, providing a very rapid, accurate reading with the reduction of the assay process steps required for a useful determination.

While the relevant prior art has been discussed in some detail above, it is useful to discuss the present concept in relation to the basic structures and processes previously known. In the test strip of conventional lateral flow technology as shown in FIG. 5, adjacent to one end 51 of a porous or chromatographic (analytical) membrane or medium 52 (the active part of the test strip) is the sample 50 introduction area 53 comprising a sample pad 54 and a conjugate pad 55. In these devices, the sample pad receives the sample and the reagents, represented by items 56, previously discussed, and the conjugate pad is the source of freely moveable colored particles 57, typically gold sols from colloidal gold, or fluorescent latex particles, which make possible the desired visual interpretations. Capture line 58 includes capture elements 59. The test strip also typically includes control line 60 and absorbent wicking pad 61.

Figure 5A:
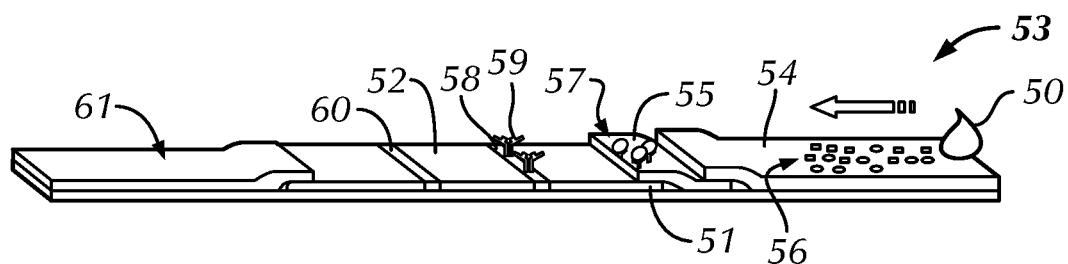
FIG. 5A is a schematic representation of a prior art lateral flow test strip before the sample and conjugate have reached a capture line.
Figure 5B:
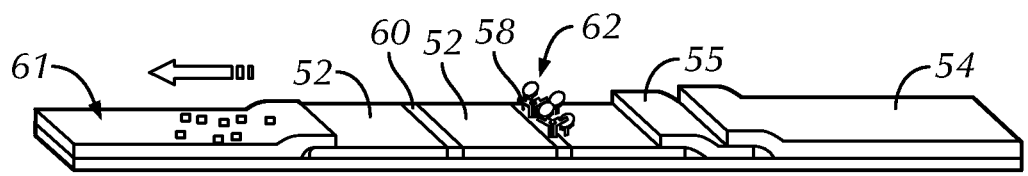
FIG. 5B is the test strip of FIG. 5A with a portion of the sample at the capture line.

As shown in FIG. 5A, sample 50 is applied, possibly by dipping or by applying a drop of sample fluid through a sample receiving port (not shown), to sample pad 54. The sample and reagents 56 combine and move by capillary action to conjugate pad 55 where they combine with conjugate therein to form a conjugate complex. Here direct contact is made between the conjugate pad and the analytical membrane, as shown by the overlapping configuration. The conjugate complex moves toward the left in this figure by capillary action to encounter capture line 58. As shown in FIG. 5B, capture elements 59 have captured the analyte of interest to provide a visual indication 62 of the analyte. Control line 60 and wicking pad 61 perform their normal functions.

Figure 4:
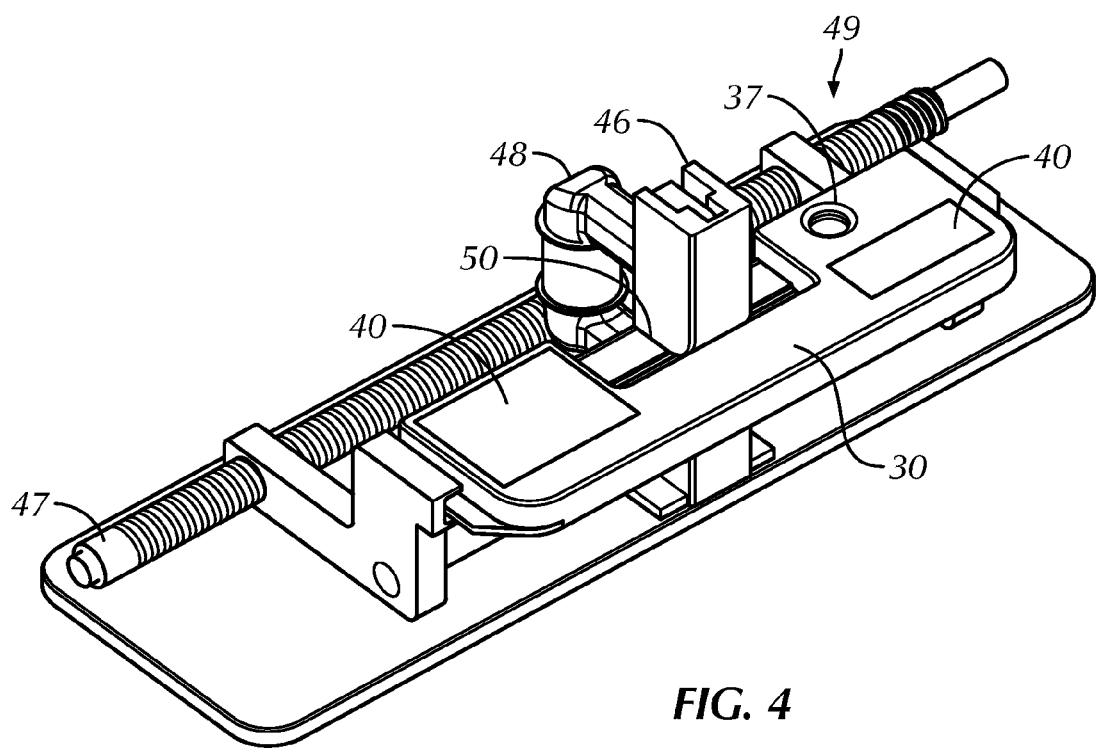
FIG. 4 shows the cassette of FIG. 1 with the strip of FIG. 2 in the gap of a magnetic field in one embodiment of an analytical instrument for reading the assay.

In some prior art test strips the movable particles 57 are magnetic elements, which may be spheres or superparamagnetic particles which are read by a magnetic reader, of the type shown in FIG. 4.

In the present concept, the moveable particles are preferably superparamagnetic particles, which label the target analytes in the sample. The sample moves through the sample pad, mixing with reagents that have a purpose of optimizing fluid flow or preventing unwanted materials from passing through the sample pad and on to the analytical membrane. The sample is then exposed to the pellicle at the bottom of the sample pad where binding occurs. There is no conjugate pad. The sample and labeled analytes then flow, due to capillary action, through a macro channel, then along the porous analytical membrane and are captured in a predefined location called a capture region or capture zone, as in the prior art. There may be more than one capture zone to enable multiplexing, which is testing for more than one type of analyte at the same time in the same test strip. Excess analytes and the sample matrix liquid continue to move on through the capture zone to the opposite end of the porous membrane, sometimes encountering a control line or zone separate from the capture zone. If a signal is detected in the control zone, the operator is assured that the analyte has passed the capture zone and that the test is functioning properly.

Typically, and optionally, a wicking pad is mounted on the distal or far end of the porous membrane to receive excess fluid. Capillary action drives the flow from the introduction at one end of the porous membrane through the entire length of the membrane. In the present apparatus a wicking pad is shown in contact with one end of the chromatographic or analytical membrane.

The benefits of the C-shaped cassette structure shown in FIG. 1, aside from the direct access to the analytical membrane, as shown in FIG. 4, relate to the convenience and simplicity of the sample introduction area, the variability of the volumes of sample introduction, and the means to wick or absorb all of the sample volume after performance of the assay. These features are accomplished by the arms or ends of the cassette, which contain the conventional materials of lateral flow technology. The sample introduction may also be sealed after application of the sample by an adhesive coated membrane.

With specific reference now to FIG. 1, generally C-shaped cassette 30 is shown in an exploded view. Multi-layered test strip 10 is positioned across the open space between the ends of the cassette, with sample and wick pads 12 and 26, respectively, fitting into elongated cavities 36 and 46 in bottom housing portion 32. Opposite ends of base member 11 of test strip 10 are gripped and tensioned by bottom housing portion 32 and top housing portion 39 to ensure proper alignment. Molded pressure pads 35, which are located just inside the cavities on the arms of the cassette, provide a specific amount of pressure to the test strip so that it performs as desired. These can be changed depending on the stack up or thickness of the particular type of assay, conventional porous membrane, or macro fluidic channel. Cover layer 24 is placed over the top of the test strip to ensure that the device is sealed and protected. A pressure on the test strip is formed when top housing portion 39 of the cassette is assembled with the bottom housing portion. The amount of pressure is one factor affecting the rate of fluid flow through the strip. In this embodiment, a desiccant (not shown) may optionally be placed within the cassette web structure, under top 39, thereby improving the storability of the assay device.

Cassette 30 may be formed of any suitable rigid material, such as plastic or the like. In a preferred embodiment, as shown in FIG. 1, additional strength to the cassette is provided by web structure 33. Other structural shapes may be employed. In addition, although the C-shaped expanse is shown, indicated by reference numeral 31, it is contemplated herein that any other shape is within the scope of the invention, as long as that shape allows the detector to access the test strip without having to pass over the cassette, the sample pad, or the wick pad.

At one end of cavity 36 is sample port 37 through housing portion 39 when the housing portions are assembled together. The sample port provides access to sample pad 12. The sample port preferably has a funnel-shaped structure extending downward and leading to and contacting the sample pad. This contact ensures that when sample fluid is added, the sample pad does not become flooded. Instead, the sample is consistently absorbed by the sample pad, thereby contributing to a uniform fluid front on the test strip.

Alignment holes 41 are configured to engage with the transport mechanism of the magnetic reader shown in FIG. 4. Labels 40 are useful but optional. They may contain human or machine readable information, or both. Such information could include calibration information for the detector/reader as well as test and date information for the user.

Figure 2:
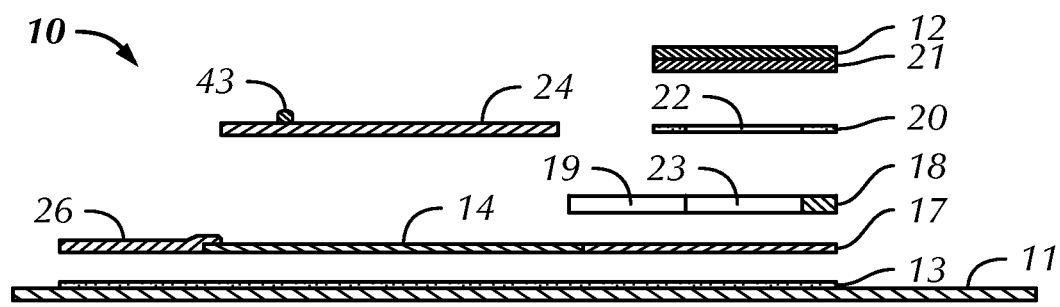
FIG. 2 is a simplified enlarged schematic partial side or sectional view of an embodiment of a test strip formed in accordance with the invention.

With reference to FIGS. 1 and 2, test strip 10 is shown, respectively, in an exploded perspective view and in a cross-sectional, partially exploded schematic view. Test strip 10 is comprised of base member 11, adhesive layer 13 (in FIG. 2), porous analytical membrane or chromatographic medium 14, and cover layer or protective membrane 24. Test line 25 and control line 28 are conventional and are typically about 0.6 to about 1.3 mm in width, with 1.0 mm being preferred. Optional wick pad 26 is shown at the distal end of the test strip. The base member can be a polyester film, such as Mylar, and the porous membrane typically is a nitrocellulose. In a conventional assembly a conjugate pad and a sample pad would have been in contact at one end of the porous membrane (see FIG. 5). In an embodiment of the present invention, a conjugate pellicle 21 on sample pad 12 and macro channel 19 in hydrophilic layer 18 provide capillary or flow communication to analytical membrane 14 from sample port 37. This is accomplished by specific components that form the direct flow assay shown in FIG. 1. The sample pad acts as the source and method of distribution of the sample together with the conjugate to the porous analytical membrane. Sample pad 12 and conjugate pellicle 21 are secured to hydrophilic layer 18 by adhesive 20, which has opening 22 to match with opening 23 in layer 18. Layer 18 is mounted on hydrophilic layer 17, which provides a floor for channel 19 which channel directly connects with opening 23 to convey the sample and conjugate complex from sample pad 12/pellicle 21 to analytical membrane 14.

The sample progresses from initial entry through sample port 37 to sample pad 12. As the fluid sample passes through sample pad 12, the sample is combined with the conjugate in pellicle 21 on the bottom of the sample pad and passes down through opening 22 in adhesive layer 20, and down to opening 23 in hydrophilic layer 18. Opening 23 is part of a key-shaped macro channel 19 which directs the fluid of the sample and conjugate from sample pad 12 along the surface of hydrophilic layer 17 to porous analytic membrane 14. Except for the sample pad, the structure and flow of the sample and conjugate in the test strip are similar to that shown in U.S. Pat. No. 7,547,557.

The structure of sample pad 12 will be described in detail below.

Filling the voids of sample pad 12, which is preferably a bibulous laminate membrane, with liquid reagents and other substances required for the analyte of interest, and then super cooling the membrane produces a solid block of membrane and reagents, providing a surface available for the formation of the frazil ice layer or pellicle 21. This provides a surface to nucleate a liquid conjugate without the liquid conjugate penetrating the previously mentioned, otherwise bibulous membrane. This results in using less conjugate and has a higher percentage of the conjugate available to combine with the sample and flow to the analytical membrane.

The void filling liquid preferably includes a fiber/membrane coating material such as polyvinylalcohol (PVA), Tris based buffer, surfactants and the like. Other materials in the liquid may include reagents used for optimum flow and performance such as non-specific binding blockers, Merquat 100, polybrene, Tween 20, trehalose sugars, agglutinators, and antibodies, among others, all known in the art. Merquat is a trademark of Lubrizol Advanced Materials and Tween is a trademark of Uniqema Americas LLC. Some of these are solvents for, or are performance enhancers, for flow of the sample or act to prevent certain components of the sample from flowing to the chromatographic medium, such as red blood cells (RBCS) and other cellular debris. Some also act as reagents to enable flow of the sample/analyte through the sample pad to maximize the rehydration of the frazil ice film and to minimize analyte retention in the sample release pad.

When the reagents are applied to a conventional conjugate pad in prior art systems by spraying or soaking, the release reagents may become inhomogeneously distributed and the conjugate can become entrapped within the conjugate pad, resulting in a relatively poor or unpredictable release and can ultimately result in an inaccurate and non-reproducible assay. The frazil ice conjugate pellicle in accordance with the present concept solves this problem.

Figure 3A:
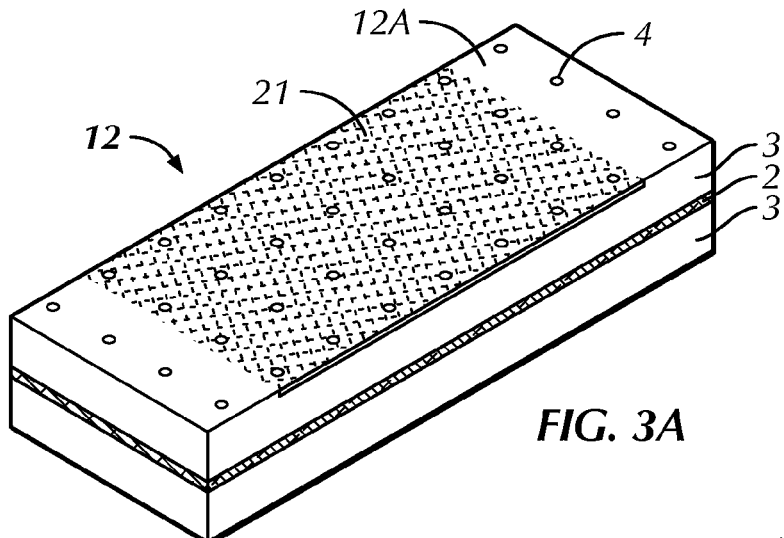
FIG. 3A shows a frazil ice pellicle on nucleation sites on a laminate used as the sample receiving membrane of the FIG. 2 test strip.

Referring now to FIG. 3, the body of sample pad 12 in one preferred embodiment is a laminate of electrically welded membranes. Polyester membranes 3 are separated by fibrous cellulose 2 and are welded, thereby forming dimples 4 on the top and bottom of the sample pad. These depressions are made up of melted material that bond the membranes, and are not holes in the sample pad but rather dimples or depressions that act as small regions which can hold reagents. The polyester membranes 3 are porous and retain the reagents used to enhance flow of the sample and, when filled and lowered to a freezing temperature, form a solid surface on which to nucleate the frazil ice conjugate film. The structure in FIG. 3A is shown in an inverted mode due to the fact that during manufacturing this would be the preferred orientation. It is to be understood that pad 12 could be a unitary structure and need not be a three layer pad, as shown.

Figure 3B:
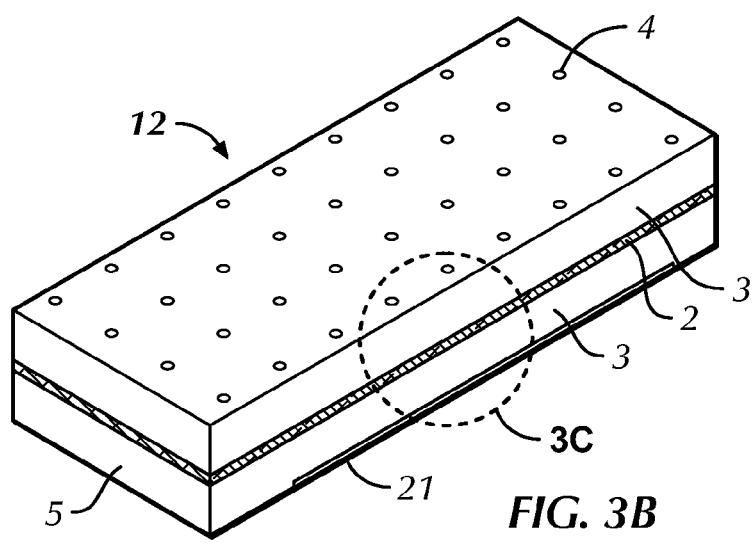
FIG. 3B is the pellicle of FIG. 3A inverted.
Figure 3C:
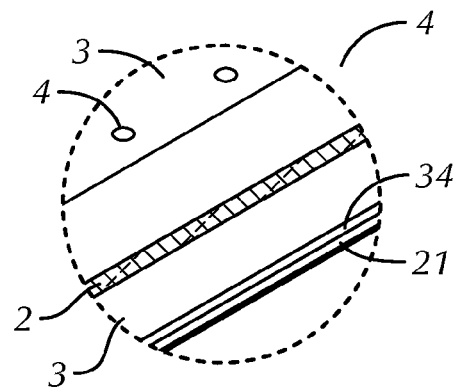
FIG. 3C is an enlarged image of a portion of the sample pad of FIG. 3B.

Frazil ice film 21 of conjugate is formed on a frozen solid surface of pad 12 which, in some embodiments, has a thin coating of hydrophobic material 34 (FIG. 3C). That coating or layer is added to the surface of pad 12 to further reduce the possibility of any interaction between the conjugate and the reagents in the sample pad body when the conjugate is applied to form pellicle 21. FIG. 3B shows the laminate in its position and orientation as it would normally exist when coupled to the complete assembly as shown in FIGS. 1 and 2.

To actually form the sample pad, after the void filling liquid, as described above, is applied to sample pad 12 to a point of saturation, the sample pad is immediately dropped to liquid nitrogen temperature of about −196° C. After reducing the sample pad temperature the void filling reagents are in a solid form and are not soluble to the liquid of the conjugate, which can be applied by spraying or by any other suitable process. The large mass of the frozen sample pad prevents the applied conjugate from interacting with the fibers of the laminate. However, a thin layer 34 of hydrophobic material may optionally be first applied to surface 12A and conjugate liquid, at about room temperature, is then sprayed onto supercooled body 12 and the frazil ice film is formed. Once at this reduced temperature, which at this point can range between about −80° C. and about −196° C., the combined membrane and conjugate pellicle unit is lyophilized (freeze dried) with a programmed temperature/pressure profile that first sublimes the hydrophobic coating (if employed), then sublimes the aqueous substances in the conjugate pellicle, and finally sublimes the aqueous portions of the reagents within the membrane of the sample pad. This freeze dried assembly is then packaged, usually with desiccant, and stored at room temperature until ready for assembly of the assay device.

While there is no critical temperature/profile contemplated for forming the frazil ice conjugate assay device, an example is included here for explanation purposes. A vacuum chamber was initially set to −40° C. and held at this temperature prior to loading low temperature aluminum plates containing frozen frazil ice pad strips. The vacuum chamber door was latched and the program was initiated. Once the program was started, the vacuum chamber was evacuated to 400 torr. The chamber shelves were held at −40° C. for 240 minutes in the primary step. The vacuum chamber was then evacuated down to 200 mtorr and held at −40° C. for an additional 100 minutes. The primary drying steps consist of raising the shelf temperature to −35° C. and holding that temperature for 130 minutes. The vacuum chamber shelves were then ramped up to −20° C. in a 65 minute time period. After the temperature ramping, the shelves temperature was held at −20° C. for an additional 220 minutes. The vacuum chamber shelves were then ramped up to 0° C. in 100 minutes and held at 0° C. for an additional 65 minutes. The vacuum chamber shelves were then brought up to +25° C. for 50 minutes, and held at 25° C. for an additional 60 minutes. The freeze dry program was halted after 17.2 hours, and vented with nitrogen gas until the chamber reached atmospheric pressure of 760 torr. The freeze dried frazil ice pads were then immediately taken to a dry room (20% rH), packaged with one-unit desiccant pouches, and heat sealed in foil pouches.

The result is a pellicle or film 21, much like a rind, of dried conjugate glazed onto the bottom side of a dry sample-receiving pad. As the sample and analyte of interest are applied and flow through the sample pad the film 21 on the bottom of the pad releases conjugate at a homogenous rate due to the exposure to all of the sample/analyte, thereby rehydrating the pellicle. At least in part due to capillary action by the analytical membrane, and optimally, by the wick pad, the conjugate is not absorbed into the sample pad and is not retained or absorbed by the fibers of the pad. This supported frazil ice pellicle does not affect the fluid flow after rehydration but allows the reagents that have been added to the sample pad to react independently of the conjugate in pellicle 21. Due to a negative pressure applied by macro channel (23, 19) via capillary flow in the test strip structure, the sample migrates to analytical membrane 14 and is chromatographed through the analytical membrane and then on to the wick pad (26) end of the diagnostic device. There is no mechanical contact between to the sample pad and the analytical membrane. Macro channel 19 guides the fluid flow from sample pad 12 to analytical membrane 14.

In this concept the conventional conjugate pad is not present; there is only a sample receiving pad with a frazil ice pellicle composed of super paramagnetic beads or particles (or other types of labels) which are coupled to antibodies. The combination of a particle or bead, and an antibody is referred to as a conjugate complex, a plurality of them being the label of the analyte. These conjugates are configured to combine with the target analytes in the sample solution in a known manner to create a sandwich assay, itself well known in the art, within the analytical capture zone 25 and the control capture zone 28. Extensions at each end of base member 11 (on which the assay strip is attached) provide means for locating the strip in the diagnostic cassette device as well as acting as a means of gripping and tensioning the strip, as is known in the prior art and has previously been described.

Although a sandwich assay has been described above, it is also contemplated herein that competitive assay techniques could be employed. The capture zone is formed by striping with antigens or antibodies, for example, as is well known. The fluid of the sample travels from right to left in FIG. 1 within the analytical membrane because of the capillary action, first by porous membrane 14 and then by wick pad 26. The wick pad enhances capillary flow by "pulling" or "driving" the fluid and allows for the total sample to be absorbed by the wick. This volume of liquid required for the assay is known as the total bed volume of the analytical membrane.

Optional cover layer 24 of the assay device may be, for example, plastic, glass, paper, or any practical combination thereof. One or more printed standard or calibration lines 43 may be situated on cover layer 24 and provide information utilized by the assay reader after the test has been accomplished. These lines 43 are contemplated to be visible, magnetic, optically reflective, or a combination thereof. These standard or calibration lines contain information that the assay reader needs, which may be, for example, calibration curves, test identification, and analytical procedures, somewhat like a bar code, and are all conventional.

While the capillary action and the existence of a capture zone 25 and control zone 28 are well known and conventional, the manner in which the described embodiments detect the presence and the quantity of the target analytes differs from prior devices. The analytical membrane is contained in a thin and sealed laminate and, as well, the fluid of the sample is directed to flow through the porous membrane to the wick pad. A significant feature of this embodiment is that the magnetic detecting device does not measure non-specifically bound magnetic labels or particles, since they have passed by the capture/control zones to a place outside of the read area of the magnetic sensing device. The capacity of the wicking pad is known so that the bed volume capacity is well absorbed and the analytical strip is the only component of the assay that the magnetic sensing device measures.

As previously stated, prior art lateral flow assays depend upon color or fluorescence to provide a visual or optical indication of the presence of target analytes in the capture zone. The ability of optical techniques to detect the presence of the target analytes is limited, as previously stated. A relatively low concentration of target analytes in the sample can result in so few captured analytes as to be optically undetectable on the surface of the porous membrane at the capture zone. Further, the optical intensity of the capture zone with the captured analytes is only a rough function of the quantity of target analytes captured. However, there is no way to accurately measure the total quantity of captured labeled analytes within the capture zone because only the surface is optically readable to a depth of about 10 microns. The analytical membrane is typically inhomogeneous and is about 200 microns in thickness. The particles of any assay travel throughout the membrane so only a small portion of the labeling particles, those near the top surfaces, are read. The present concept provides greatly enhanced sensitivity and quantitative accuracy because the magnetic labeled analytes in the capture zone are detectable by a suitable magnetic detector to the extent of the target analytes within the entire volume of the capture zone, not just at the surface.

Additional features may be added, including additional capture zones (two are shown in the figures) and additional control lines. There could be several capture zones and equivalent control lines.

With reference to FIG. 4, for the embodiments disclosed herein, the test strip of cassette 30 is inserted into gap 50 of reader 49. Accordingly, sensor coils are positioned on both sides of the test strip when the test strip is introduced. One advantage of this arrangement is that the magnetic measurement is minimally sensitive to the vertical position of the test strip within the gap in the coil. An exemplary reader and the manner of using it are described in U.S. Pat. No. 7,323,139.

It is contemplated that test strip 10, primarily consisting of the porous analytical membrane and the sample handling elements in FIGS. 1 and 2, is made sufficiently rigid to need a minimum support from the ends of the cassette. Such a configuration would make the assay device easy to handle and to archive. FIG. 1 shows how the test cassette, comprised of the top cover, test strip, and bottom cover, is assembled. This completed test region (that portion of the test strip exposed in C-shaped gap 31) can be typically about 15 to about 50 mm wide (across gap 31), and strip 10 is only about 150 to about 500 microns thick. This strip is easily fed into reader 49 for a digital readout (not shown), which may be shown on a screen or printed on paper in any desired form by the user.

Since the test strip may actually touch the detector, as shown in FIG. 4, without the optional protective cover surface 24 the porous nitrocellulose membrane could be damaged by rubbing across the detector, thereby possibly producing incorrect or unreliable readings, or both. In addition, cover 24 protects the detector coils from being contaminated from assay to assay. Although being very thin, in the range of about 25 to about 100 microns in thickness, the cover protects against physical damage and environmental contamination as well as providing precise positioning for accurate electromagnetic readings.

What is claimed is:

1. A test strip for an assay device, the test strip comprising:
    an elongated porous membrane having a top surface and a bottom surface, having a proximal end and a distal end, and having at least one test line;
    a sample pad adjacent the proximal end of said porous membrane, said sample pad having a first surface and a second surface, said first surface being parallel with and oriented in the same direction as said bottom surface of said porous membrane, said sample pad being impregnated to a condition of approximate saturation with a selective mix of at least two of water, buffers, protectants, proteins, or surfactants and then being frozen at about −80° C. or below;
    a conjugate pellicle on said first surface of said previously frozen sample pad, said sample pad and said conjugate pellicle having been lyophilized; and
    means for providing fluid communication between said conjugate pellicle and said porous membrane.

2. The test strip of claim 1, and further comprising a wick pad on the distal end of said porous membrane.

3. The test strip of claim 1, wherein said means for providing fluid communication comprises:
    a hydrophilic layer formed with a macro channel beneath said conjugate pellicle on said sample pad, said macro channel having a closed end and an open end for fluid communication with said porous membrane.

4. The test strip of claim 1, wherein said sample pad comprises:
    a fibrous cellulose layer; and
    a polyester membrane on either side of said fibrous cellulose layer.

5. The test strip of claim 1, and further comprising a protective membrane on top of said porous membrane and covering said at least one test line.

6. The test strip of claim 3, and further comprising an elongated base member to which said porous membrane and said fibrous cellulose layer are secured in adjacent planar relationship.

7. A process for making an assay test strip comprising:

preparing a sample pad by impregnating therein a selective mix of at least two of water, buffers, protectants, proteins, and surfactants to a condition of approximate saturation;

freezing the thus prepared sample pad at about −80° C. or below for a first period of time;

maintaining the sample pad at a temperature between about −80° C. and about −196° C.; then applying an aqueous conjugate solution to one surface of the sample pad so that it nucleates and forms a pellicle on that surface;

lyophilizing the sample pad and conjugate pellicle at about −80° C. or below to remove aqueous aspects in and on the sample pad; and increasing the temperature of the lyophilized sample and conjugate pellicle pad to room temperature.

8. The process of claim 7, and comprising the further steps of:

mounting the lyophilized sample pad and conjugate pellicle on a hydrophilic layer having a macro channel opening into one end thereof;

mounting the hydrophilic layer, sample pad, and conjugate pellicle on an elongated base member; and mounting an elongated analytical membrane on the base member adjacent to the open end of the macro channel, thereby forming the test strip.

9. The process of claim 7, wherein the sample pad freezing temperature is about −196° C.

10. The process of claim 8, and comprising the further step of mounting the test strip to a cassette in preparation for conducting an assay when sample material has been applied to the test strip.

11. An assay device comprising:

a cassette having a body and two arms extending from opposite ends thereof to form a C-shaped opening therebetween;

a test strip affixed to said arms and extending across the C-shaped opening, said test strip comprising:

an elongated base member;

an elongated porous membrane having a top surface and a bottom surface, having a proximal end and a distal end, and having at least one test line and at least one control line spaced in a downstream direction from the test line;

a sample pad adjacent the proximal end of said porous membrane, said sample pad having a first surface and a second surface, said first surface being parallel with and oriented in the same direction as said bottom surface of said porous membrane, said sample pad being impregnated to a condition of approximate saturation with a selective mix of at least two of water, buffers, protectants, proteins, or surfactants and then being frozen at about −80° C. or below;

a conjugate pellicle on said first surface of said previously frozen sample pad, said sample pad and said conjugate pellicle having been lyophilized; and means for providing fluid communication between said conjugate pellicle and said porous membrane.

* * * * *